US00PP15981P2

(12) United States Plant Patent
Warner

(10) Patent No.: US PP15,981 P2
(45) Date of Patent: Sep. 20, 2005

(54) ROSE PLANT NAMED 'CHEWGROUND'

(50) Latin Name: *Rosa hybrida*
Varietal Denomination: Chewground

(75) Inventor: Christopher Hugh Warner, Greenfields Brocton (GB)

(73) Assignee: Spring Meadow Nursery Inc., Grand Haven, MI (US)

( * ) Notice: Subject to any disclaimer, the term of this patent is extended or adjusted under 35 U.S.C. 154(b) by 20 days.

(21) Appl. No.: 10/882,951

(22) Filed: Jul. 1, 2004

(51) Int. Cl.[7] ..... A01H 5/00
(52) U.S. Cl. ..... Plt./107
(58) Field of Search ..... Plt./107, 148

(56) References Cited

PUBLICATIONS

UPOV–ROM GTITM, Plant Variety Database, 2004/04, GTI Jouve Retrieval Software, Citation for Rosa 'Chewground'.*

* cited by examiner

*Primary Examiner*—Anne Marie Grunberg
*Assistant Examiner*—June Hwu
(74) *Attorney, Agent, or Firm*—C. A. Whealy

(57) ABSTRACT

A new and distinct cultivar of Rose plant named 'Chewground', characterized by its low mounding plant habit; glossy dark green-colored leaflets; vigorous and freely branching growth habit; red purple-colored single flowers; resistance to Black Spot and mildews; and good garden performance.

2 Drawing Sheets

Botanical classification/cultivar designation: *Rosa hybrida* cultivar Chewground.

BACKGROUND OF THE INVENTION

The present Invention relates to a new and distinct cultivar of Rose plant, botanically known as *Rosa hybrida*, commercially used as cut stems with fruits or hips, and hereinafter referred to by the name 'Chewground'.

The new Rose is a product of a planned breeding program conducted by the Inventor in Newport, Shropshire, United Kingdom. The objective of the breeding program was to develop new shrub Rose varieties with disease resistance and attractive flower coloration.

The new cultivar originated from a cross-pollination made by the Inventor in 1994 of the Rose cultivar Grouse, not patented, as the female, or seed, parent with the Rose cultivar Yesterday, not patented, as the male, or pollen, parent. The cultivar Chewground was discovered and selected by the Inventor in 1995 as a single flowering plant within the progeny of the stated cross-pollination in a controlled environment in Newport, Shropshire, United Kingdom.

Asexual reproduction of the new Rose by softwood cuttings at Newport, Shropshire, United Kingdom since 1995, has shown that the unique features of this new Rose are stable and reproduced true to type in successive generations of asexual reproduction.

SUMMARY OF THE INVENTION

The following traits have been repeatedly observed and are determined to be the unique characteristics of 'Chewground'. These characteristics in combination distinguish 'Chewground' as a new and distinct cultivar:

1. Low mounding plant habit.
2. Glossy dark green-colored leaflets.
3. Vigorous and freely branching growth habit.

4. Red purple-colored single flowers.
5. Resistant to Black Spot and mildews.
6. Good garden performance.

Plants of the new Rose are most similar to plants of the parent cultivars. Compared to plants of the female parent, the cultivar Grouse, plants of the new Rose flower only one time per season whereas plants of the cultivar Grouse flower recurrently. Plants of the new Rose and the male parent, the cultivar Yesterday, differ in plant form as plants of the cultivar Yesterday are more upright and larger. In addition, plants of the new Rose are more fragrant than plants of the cultivar Yesterday.

Plants of the new Rose can be compared to plants of the Rose cultivar Flower Carpet, disclosed in U.S. Plant Pat. No. 7,282. In side-by-side comparisons conducted in Grand Haven, Mich., plants of the new Rose differed from plants of the cultivar Flower Carpet in the following characteristics:

1. Plants of the new Rose were more vigorous than plants of the cultivar Flower Carpet.
2. Plants of the new Rose had a more intense flower color than plants of the cultivar Flower Carpet.
3. Plants of the new Rose were more fragrant than plants of the cultivar Flower Carpet.

BRIEF DESCRIPTION OF THE PHOTOGRAPHS

The accompanying colored photographs illustrate the overall appearance of the new Rose, showing the colors as true as it is reasonably possible to obtain in colored reproductions of this type. Colors in the photographs may differ slightly from the color values cited in the detailed botanical description which accurately describe the colors of the new Rose.

The photograph on the first sheet comprises a side perspective view of a typical plant of 'Chewground'.

The photograph on the second sheet is a close-up view of typical flowers of 'Chewground'.

DETAILED BOTANICAL DESCRIPTION

The new Rose has not been observed under all possible environmental conditions. The phenotype may vary somewhat with variations in environment such as temperature and light intensity, without, however, any variance in genotype.

The aforementioned photographs, following observations and measurements describe plants grown in Grand Haven, Mich., in an outdoor nursery and under commercial production practices. Plants were about four years old. The photographs and description were taken during the late summer. In the follwing description, color references are made to The Royal Horticultural Society Colour Chart, 1995 Edition, except where general terms of ordinary dictionary significance are used.

Botanical classification: *Rosa hybrida* cultivar Chewground.

Parentage:

*Female, or seed, parent.*—*Rosa hybrida* cultivar Grouse, not patented.

*Male, or pollen, parent.*—*Rosa hybrida* cultivar Yesterday, not patented.

Propagation:

*Type.*—Softwood cuttings.

*Time to initiate roots.*—About 12 days at 25° C.

*Time to produce a rooted young plant.*—About three months at 25° C.

*Root description.*—Freely branching; medium thickness; soft brown in color.

Plant description:

*Plant form.*—Low mounding perennial shrub.

*Growth habit.*—Vigorous growth habit. Freely branching habit; about 43 lateral branches per plant; dense and bushy growth habit.

*Plant height.*—About 40 cm.

*Plant width* (*spread*).—About 1.5 meter.

*Lateral branches.*—Length: About 60 cm. Diameter: About 4 mm. Internode length: About 2.7 cm. Strength: Strong. Angle: Outwardly arching. Texture: Smooth, glabrous. Color: 138A. Thorns: Density: Dense. Shape: Triangular with sharp acuminate apices. Height: About 6 mm. Diameter, at base: About 2 mm. Color: 141D overlain with 48A.

*Foliage description.*—Leaves alternate; compound with about seven leaflets. Leaf length: About 2.5 cm. Leaflet width: About 1.3 cm. Leaflet shape: Ovate to lanceolate. Leaflet apex: Acute. Leaflet base: Obtuse. Leaflet margin: Serrate. Leaflet texture, upper and lower surfaces: Smooth, glabrous. Leaflet venation pattern: Pinnate. Leaflet color: Developing leaflets, upper surface: 137A. Developing leaflets, lower surface: 135C. Fully expanded leaflets, upper surface: 135A; glossy. Fully expanded leaflets, lower surface: 135C. Venation, upper surface: 135A. Venation, lower surface: 135C. Leaf petiole: Length: About 1.1 cm. Diameter: About 3 mm by 2 mm. Texture, upper and lower surfaces: Smooth, glabrous. Color, upper and lower surfaces: 135C.

Flower description:

*Flower type and habit.*—Red purple-colored single rotate flowers arranged in terminal clusters with about four flowers per cluster. Flowers not persistent. Flowers face mostly outwardly.

*Natural flowering season.*—Plants flower in the landscape from June until frost in Grand Haven, Mich.; during this period flowering not recurrent.

*Postproduction longevity.*—Flowers typically last one to two weeks on the plant as well as a cut flower.

*Fragrance.*—Very fragrant; typical of *Rosa*; sweet, pleasant.

*Flower buds.*—Height: About 1.3 cm. Diameter: About 6 mm. Shape: Lanceolate. Color: 63A.

*Flowers.*—Diameter: About 5 cm. Depth: About 1.2 cm.

*Petals.*—Quantity per flower: Five in a single whorl. Length: About 2.9 cm. Width: About 2 cm. Shape: Obovate. Apex: Obtuse to retuse. Base: Attenuate. Margin: Entire. Texture, upper and lower surfaces: Smooth, glabrous. Color: Developing and fully expanded, upper surface: 66A. Developing and fully expanded, lower surface: 66C; color becoming closer to 66D with development.

*Sepals.*—Quantity per flower: Five. Length: About 1.5 cm. Width: About 4 mm. Shape: Roughly lanceolate. Apex: Acute. Base: Fused. Margin: Entire. Texture, upper and lower surfaces: Smooth. Color: Developing, upper surface: 143C. Developing, lower surface: 143B. Fully expanded, upper surface: 143C. Fully expanded, lower surface: 143A.

*Peduncles.*—Length: About 2.5 cm. Diameter: About 1.5 mm. Orientation: About 20° from vertical. Strength: Strong. Color: 143B.

*Reproductive organs.*—Stamens: Quantity per flower: About 50. Anther shape: Oblong. Anther length: Less than 1 mm. Anther color: 22A. Pollen amount: Moderate. Pollen color: 22A. Pistils: Quantity per flower: About 10. Pistil length: About 1 mm. Stigma shape: Oval. Stigma color: 14B. Style length: About 3 mm. Style color: 14D. Ovary color: 143C.

*Fruits.*—Quantity per plant: About 129. Type: Fleshy hip. Shape: Roughly ovoid. Length: About 1 cm. Diameter: About 6 mm. Texture: Smooth, glabrous. Color: 143C.

*Seeds.*—Quantity per fruit: About eight. Length: About 1.5 mm. Diameter: About 1 mm. Color: 143D.

Pathogen/pest resistance: Plants of the new Rose have been observed to be resistant to Black Spot and mildews. Plants of the new Rose have not been observed to be resistant to pests and other pathogens common to Roses.

Garden performance: Plants of the new Rose have been observed have good garden performance and to tolerate rain, wind and temperatures ranging from −25 to 30° C.

It is claimed:

1. A new and distinct cultivar of Rose plant named 'Chewground', as illustrated and described.

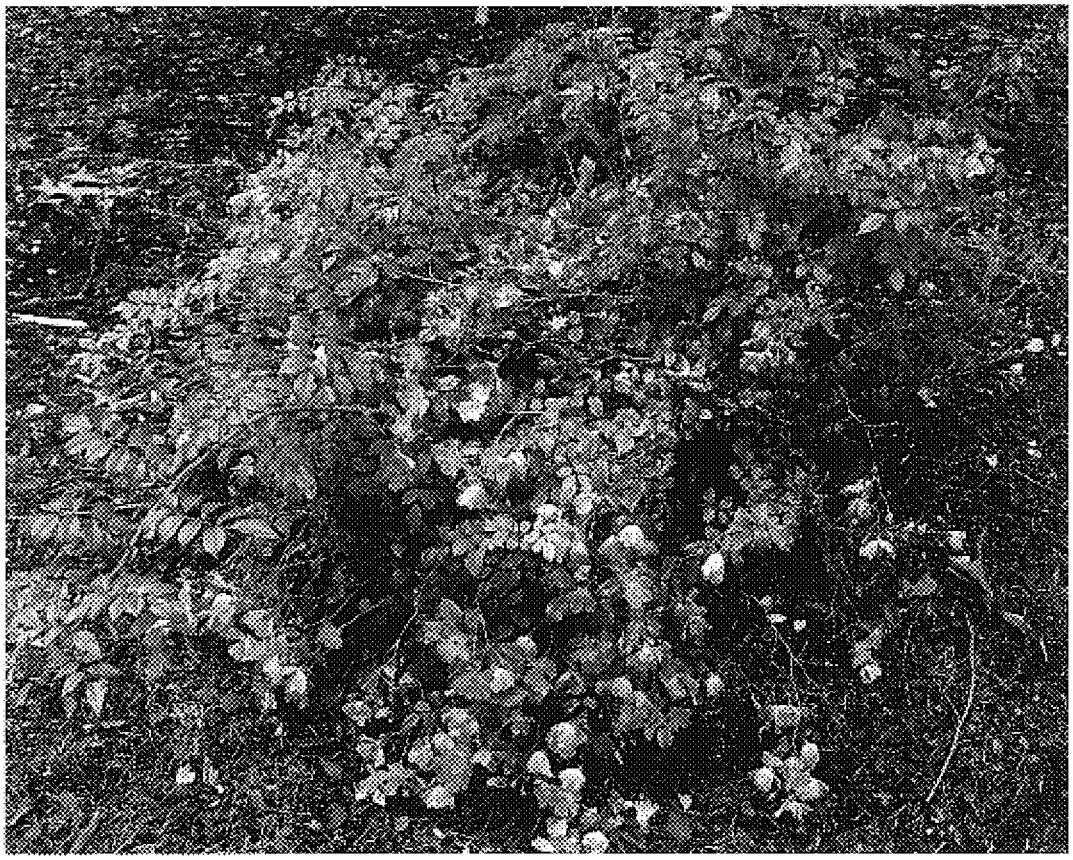

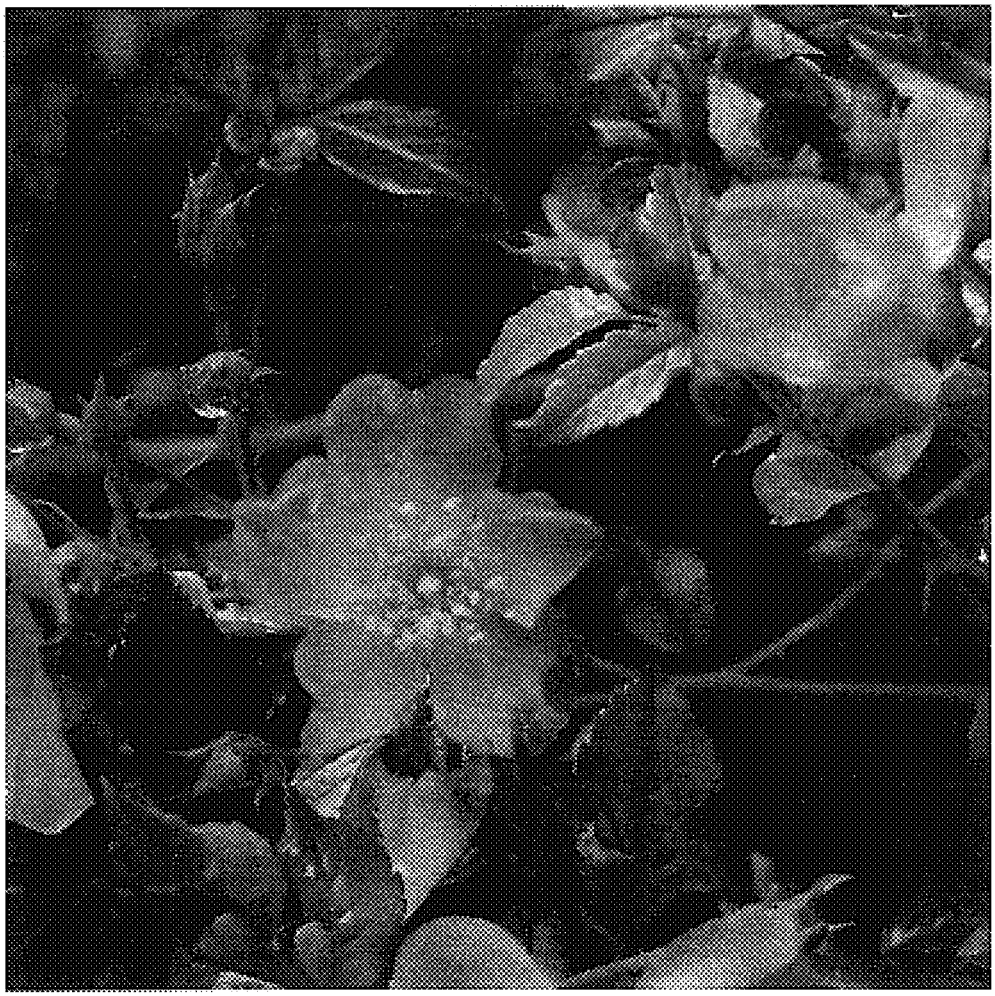

* * * * *